United States Patent [19]

Pitchford, Jr.

[11] 4,248,226

[45] Feb. 3, 1981

[54] AUTOMATIC DOUCHE MECHANISM

[76] Inventor: Robert L. Pitchford, Jr., 2892 Bayard St., East Point, Ga. 30344

[21] Appl. No.: 83,690

[22] Filed: Oct. 11, 1979

[51] Int. Cl.³ .............................................. A61M 3/00
[52] U.S. Cl. .................................................... 128/229
[58] Field of Search .................. 128/229, 227, 251, 66

[56] References Cited

U.S. PATENT DOCUMENTS

| 1,973,262 | 9/1934 | McQueen, Jr. | 128/229 |
| 2,157,756 | 5/1939 | Irwin | 128/229 |
| 2,241,823 | 5/1941 | McFarland et al. | 128/229 |
| 2,522,122 | 9/1950 | Kertesz | 128/229 |
| 2,922,421 | 1/1960 | Endrezze et al. | 128/227 |

Primary Examiner—John D. Yasko
Attorney, Agent, or Firm—Paul H. Ware

[57] ABSTRACT

An automatic douche device in which a douche can be administered for extended periods and in which medication can be metered into the main douche fluid flow even when the device of the invention is in operation. The device in adaptable for water inlet from a conventional water faucet or from a showerhead.

2 Claims, 8 Drawing Figures

AUTOMATIC DOUCHE MECHANISM

BACKGROUND OF THE INVENTION

1. Field of the Invention

This invention relates generally to douche mechanisms and more particularly to wall mounted, medication dispensing douche mechanisms for home or institutional use.

2. Description of the Prior Art

Douche mechanisms are known in which the force of gravity is utilized to effect a flow of fluid forceful enough to cleanse. Some of the devices are simple to operate, but by the same token, they also lack some very desirable features, for example, the provision of medication dispensation in a convenient manner. Thus, the basic types of douche mechanisms are well known in the art. Many types have been developed and have been in clinical and home use for many years. Most of these prior art devices, however, have met special needs as presented by specific problems and have thus served narrow purposes. Some of these prior art devices have been described in the following listed patents that were brought to the attention of the applicant through a novelty search conducted in the United States Patent and Trademark Office:

| 1. | Title: | WALL MOUNTED HYGIENIC DEVICE |
| --- | --- | --- |
| | U.S. Pat. No.: | 4,000,742 |
| | Patentee: | Edward F. DiGiacomo |
| 2. | Title: | MULTIPURPOSE HYGIENIC KIT |
| | U.S. Pat. No.: | 3,870,045 |
| | Patentee: | Curtis M. Vaughan |
| 3. | Title: | DOUCHE APPARATUS |
| | U.S. Pat. No.: | 3,533,409 |
| | Patentee: | William Greer |
| 4. | Title: | MEANS FOR TREATING SURFACE WOUNDS |
| | U.S. Pat. No.: | 3,288,140 |
| | Patentee: | J. J. McCarthy |
| 5. | Title: | LOW PRESSURE DOUCHE DEVICE WITH MEDICAMENT MIXING CONTAINER |
| | U.S. Pat. No.: | 3,254,647 |
| | Patentee: | Vernon J. Vogel |
| 6. | Title: | MEDICAL APPLICATOR |
| | U.S. pat. No.: | 3,078,848 |
| | Patentee: | A. H. Milbert |
| 7. | Title: | DOUCHE AND SYRINGE |
| | U.S. Pat. No.: | 1,680,762 |
| | Patentee: | J. W. Butler et al |
| 8. | Title: | DISINFECTING DEVICE |
| | U.S. Pat. No.: | 641,548 |
| | Patentee: | W. H. Rose |

Many of these prior art devices have had defects which have made them inappropriate and sometimes even dangerous to use in some cases.

It would thus be a great advantage to the art to provide an automatic douche mechanism that is reliable in its operation.

Another advantage would the provision of such a device in a simple and economical package.

A further advantage would be the provision of such a device wherein the administration of the douche so provided could be repeated without the necessity of refilling for purposes of medication dispensation.

A still further desirable advantage would be the provision for automatic refilling of the device by means of its own internal mechanism.

SUMMARY OF THE INVENTION

In light of the advantages sought to be accomplished in the instant invention it is thus an object of the present invention to provide an automatic douche mechanism that is reliable in its operation.

Another object sought to be provided in the instant invention is the provision of such a device as noted above in a simple and economical package.

A further object of the instant invention is the provision of such a device wherein the administration of the douche so provided may be repeated without the necessity of refilling for purposes of medication dispensation.

A still further object of the invention is the provision for automatic refilling of the douche device by means of its own internal mechanism.

In the accomplishment of these and other objects, an automatic douche mechanism is provided in which the device may be connected to a conventional bathtub faucet or to a conventional shower inlet. The body of the device, somewhat corresponding to the conventional douche bag, excepts water from a conventional home or other water source and automatically shuts off the filling water when full. While the filling process is taking place, the medication, if any is desired, can be dispensed into the fill water so as to be thoroughly mixed when the douche is to be actually administered. When the device becomes empty, the filling cycle automatically starts again with the dispensation of medication also automatically taking place. The cycle of fill, dispense medication, douche, can be repeated as many times as the user may desire merely by that users allowing the water source to remain incident in its inlet tubes. To shut down the device, it is only necessary to shut down the source of water pressure at the inlet tube and close the clamp provided for that purpose.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings wherein like reference characters refer to like parts throughout and in which.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figures 1, 2:
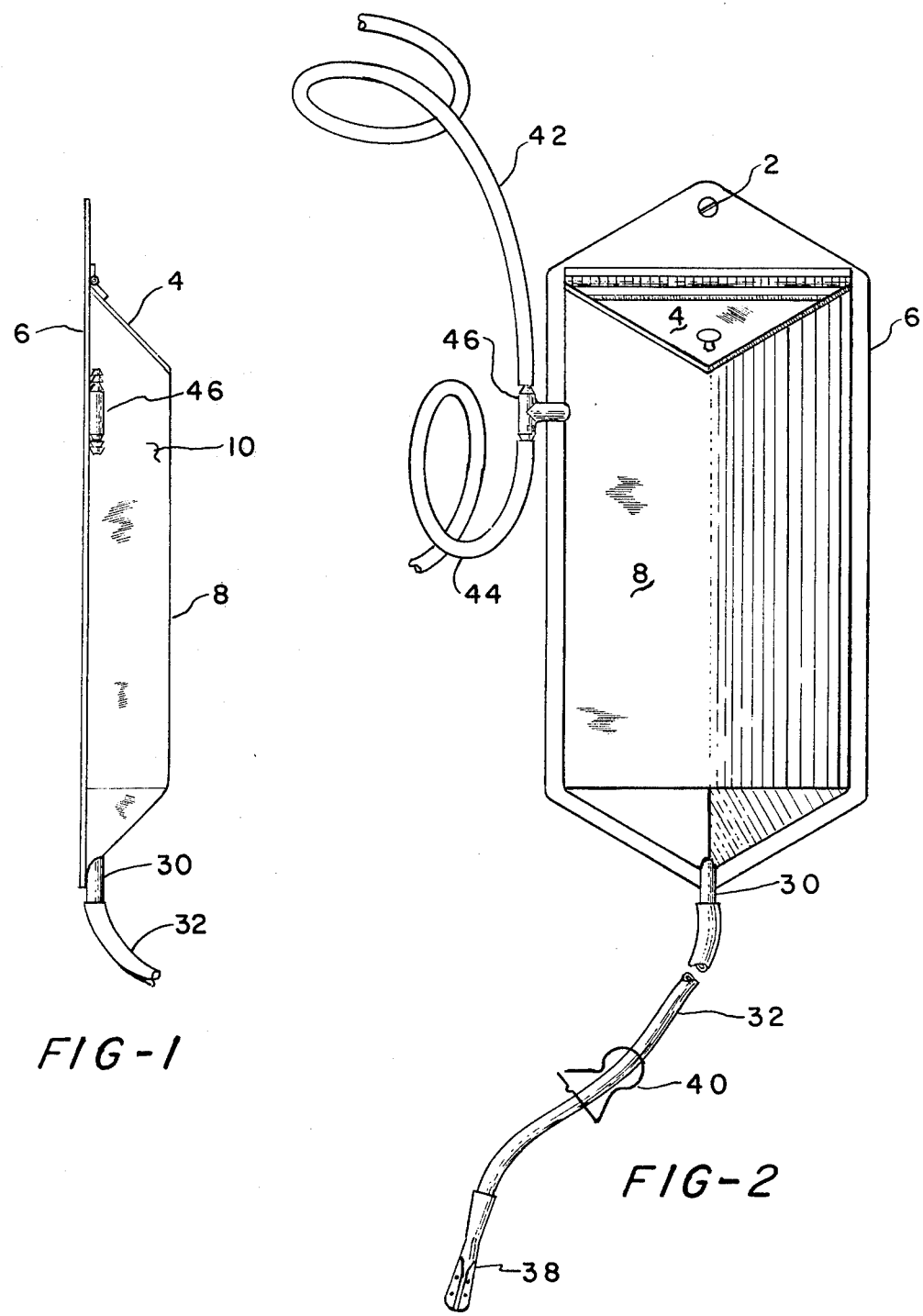
FIG. 1 is a profile view of the device of the invention.
FIG. 2 is a frontal elevation of the device showing exterior detail.

Referring to FIG. 1 with greater particularity, a profile view of the device is indicated generally by the numberal 10. The device is shown as upright with its rear wall as if mounted against a wall in the home. The hinged top 4 would be lifted in order to place medication in the medication dispenser 74. The front of the body 8 would be toward the user. The fluid outlet 30 is shown connected to flexible tube 32.

In FIG. 2, the first inlet tube 42 is shown as attached to T-46 as is a second inlet tube 44, that may be used as an inlet from a bathroom faucet or the like. Flexible tube 32 is shown as having a conventional clamp 40 used to cut off the supply of douche fluid to conventional nozzle 38.

Figure 3:
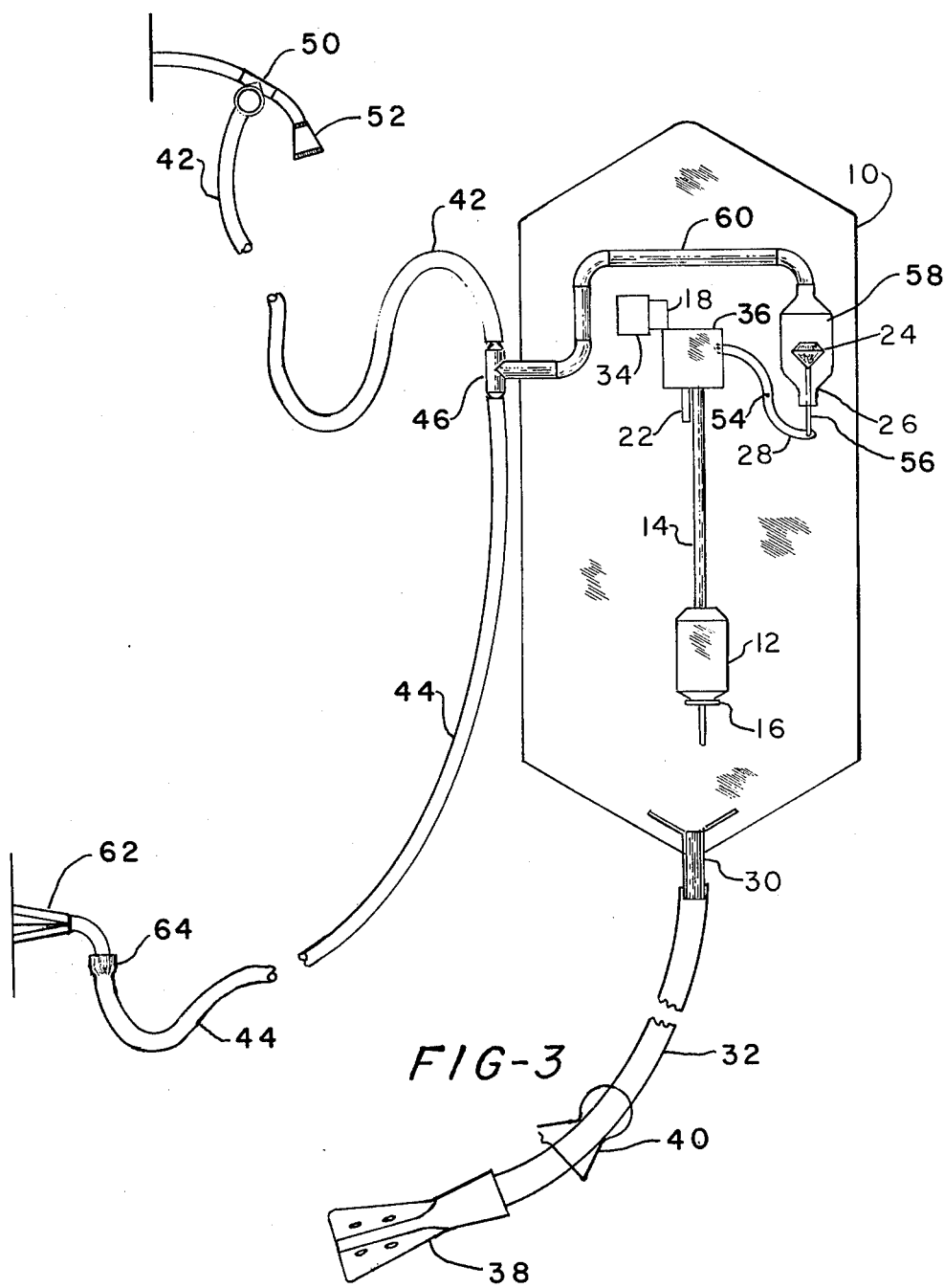
FIG. 3 is a frontal elevation of the device showing some of the details of the interior thereof.

The frontal elevation of FIG. 3 shows greater detail of the interior of the device. A diverter valve 50 is shown as being connected to a conventional showerhead 52 and accommodating the first inlet tube 42 which connects to the T-46. A bathtub faucet 62 is shown connected to adapter 64 which connects to second inlet tube 44 also connected to T-46. T-46 connects by its shank member to internal piping 60 which in turn connects into valve body 58. Valve body 58 comprises plunger valve 24 and valve seat 26. Valve 26 is connected to control arm 28 by means of valve stem 56. Lever pin 54 defines a midpoint for control arm 28 being thence connected to accuating float member 36. A float 12, limited as to its downward position by float limit stop 16 is operable to slide upward on rod 14 under the influence of a filling fluid so as to operate release pin 22 which in turn causes retraction of control pin 18 situated in spring housing 34.

Figure 4:
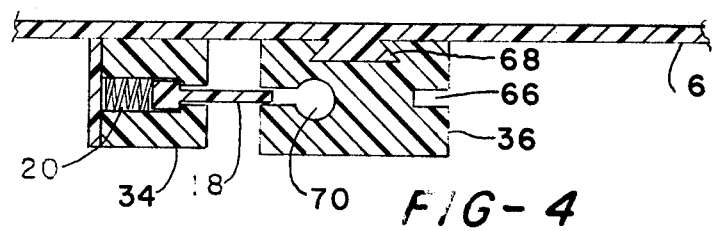
FIG. 4 is a top detail view of some of the mechanism of the device.

Referring now to FIG. 4 a top detailed view of spring housing 34 and control pin 18 is presented in a manner that may further explain operation of the device. Spring housing 34 contains a spring 20 influencing control pin 18. Actuating float mechanism 36 may be seen to have a circular slot aperture 70 and a rectangular slot 66. A trapezoidal guideway 68 forms a part of the rear wall of the body of the device.

Figures 5, 7:
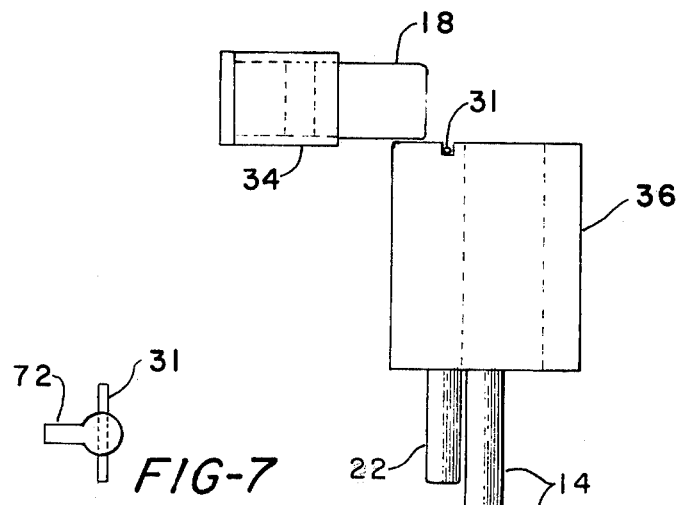
FIG. 5 is a side elevation useful to explain some of operation of the device.
FIG. 7 is a top view of the detail of FIG. 6.
Figure 6:
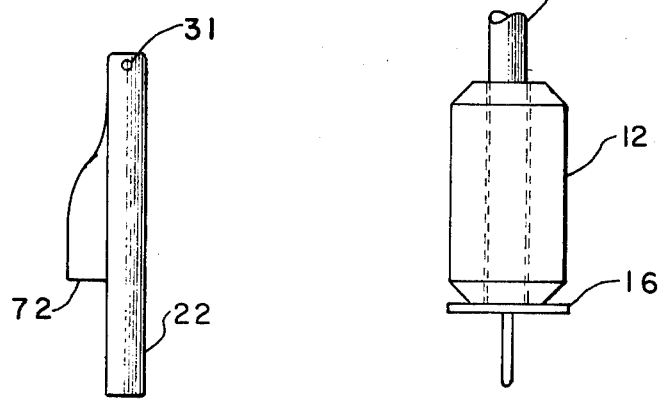
FIG. 6 is a detail of an element of the apparatus.
Figure 8:
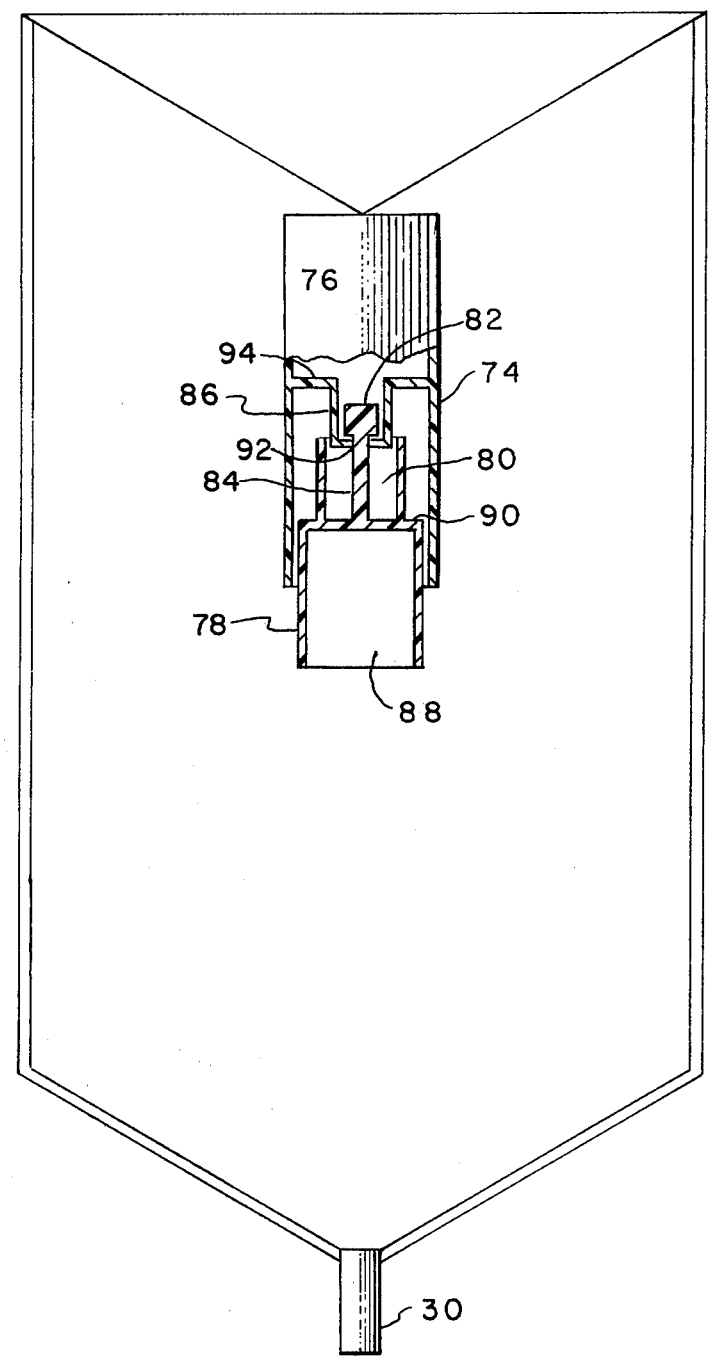
FIG. 8 is a partial cross section helpful in explaining the operation of the medication dispensing provision of the device.

Referring now to FIGS. 5, 6 and 7, the general operation of the device will be explained. FIG. 6 is seen to be a release pin 22 having a control pin actuater 72 and a retaining pin 31. FIG. 7 is a top view of the detail of FIG. 6. In operation as filling water comes through the valve body 48 (FIG. 3) the float 12 begins to rise off of float limit stop 16 and to travel up along rod 14. Control pin 18, being in contact with actuating float member 36, prevents the rise of actuating float member for the moment. As float 12 continues it rise along rod 14, it eventually comes into contact with release pin 22 and pushes that member upward. As release pin 22 travels upward, control pin actuator 72 forces control pin 18 toward the left by means of its travel along the ramp shown as a portion of control pin actuator 72. When control pin 18 is fully retracted against spring 20 (FIG. 4), actuating float member 36 may rise upward thus operating control arm 28 (FIG. 3) so as to cause plunger valve 24 to seat against valve seat 26 thus shutting off the flow of water into the device. Fluid contained in the device may now be dispensed through outlet 30 and flexible tube 32 by opening conventional clamp 40 thus allowing the fluid to be dispensed through conventional nozzle 38. As the fluid level lowers in the body of the device, float 12 descinds the rod 14 to float limit stop 16. When float 12 comes into coincidence with float limit stop 16 actuating float member 36 is pulled downward by the weight of the float 12 thus allowing control pin 18 to assume an extended position under the action of spring 20. The above described motion operates control arm 28 so as to raise plunger valve 24 from its seated position on valve seat 26 thus permitting the flow of water through the valve body 58. If now conventional clamp 40 is closed, the refilling of the device may take place and the complete cycle may be begun again. If conventional clamp 40 is not closed, the flow of filling water could be allowed to continue through outlet 30, however, such is not contemplated as an effective nor effecient way of operating the apparatus of the intention because of the medication provision incorporated into the device which will now be described with reference to FIG. 8.

Outer cylinder 76 is designed to contain the medication to be dispensed with the douche. Stop member 82 forms a fluid tight connection with the aperture of inner cylinder 86. Thus none of the medication contained in outer cylinder 76 can escape into dosimeter cylinder 80 as long as stop member 82 is in the position with respect to aperture 92 as shown in the figure. Operation of the medication dispensing provision of the device may be explained as follows:

As the fill water rises in the body of the device, innercylinder 78 floats upward within the confines of outer cylinder 76. As innercylinder 78 begins to rise, stop member 82 attached at one end of dispenser rod 84 also beings an upward movement. It will be noted that the fluid tight connection between stop member 82 and aperture 92 has now been disturbed so as to permit fluid medication contained in outer cylinder 76 to flow into dosimeter cylinder 80. The fluid that flows into dosimeter cylinder 80, however, can overflow into the lower part of outer cylinder 76 and outward into the body of the device. Such flow will continue until innercylinder 88 completes its upward travel whereupon it forms a fluid tight connection with aperture 92. The device will remain in the just described configuration until the fluid level in the device is lowered enough to permit innercylinder 88 to fall to the position shown in the illustration.

Thus there has been described an AUTOMATIC DOUCHE MECHANISM that will permit the continuous application of a medicated douche. Great improvements in reliability, flexibility, maintainability, ease of operation and safety have been provided through the novel advantages of the invention.

It is pointed out that although the present invention has been shown and described with reference to particular embodiment, nevertheless, various changes and modifications obvious to one skilled in the art to which the invention pertains are deemed to lie within the purview of the invention.

What is claimed and desired to be secured by Letters Patent of the United States is:

1. An automatic douche mechanism comprising:
a reservoir having a front a rear wall and a top;
means for receiving water as a component of a douche fluid from conventional domestic sources into said reservoir;
dispensing outlet means attached to said reservoir so as to accept and dispense said douche fluid therefrom;

a flexible tube attached to said dispensing outlet means for conducting said douche fluid to a user's body;

a clamp attached to said flexible tube near to said dispensing outlet and operable to interrupt the flow of said douche fluid to said user's body;

a nozzle attached to said flexible tube at an end thereof and distal to said dispensing outlet means so as to be separated therefrom by said clamp;

a valve fluidically communicating with said means for receiving water from coventional domestic sources, said valve having:

a valve body;

plunger valve means in said valve body;

a valve stem in said valve body one end of which is attached to said plunger valve means;

a valve seat operable to accept seating of said plunger valve thereupon;

a control arm attached to the other end of said valve stem operable to seat and unseat said plunger valve to said valve seat;

actuating float and rod means for operating said plunger valve means, said float and rod means having:

a rod also having an uppermost end attached to an actuating float number, itself attached to said control arm;

a float limit stop attached near the lowermost end of said rod;

a float slideably attached to said rod and constrained by said float limit stop;

control mechanism constraining said actuating float and rod means comprising:

a spring loaded control pin engageable upon a top surface portion of said actuating float member so as to constrain its upward motion;

a spring housing retaining a spring for spring loading said spring loaded control pin;

releasing mechanism for releasing said constraint imposed upon said actuating float member by said spring loaded control pin so as to permit upward motion of said actuating float member including a release pin having a control pin actuator and a retaining pin.

2. The automatic douche mechanism of claim one further including medication dispensing means comprising;

a first inner cylinder having an open end and a closed end;

a dispenser rod having one of its ends attached at the closed end said first inner cylinder;

a dosimeter cylinder attached to said closed end of said 1st inner cylinder so as to enclose said dispenser rod;

a second inner cylinder open at one end and having an aperture at one end thereof for accepting the other end of said dispensing rod therethrough;

a stop member operable to retain said other end of said dispensing rod in the interior of said second inner cylinder;

an outer cylinder having an interior annular member attached to the open end of said second inner cylinder.

* * * * *